(12) United States Patent
Doyle, Jr.

(10) Patent No.: US 6,633,378 B2
(45) Date of Patent: Oct. 14, 2003

(54) SCANNING SYSTEM

(75) Inventor: James L. Doyle, Jr., Renton, WA (US)

(73) Assignee: Lotis Tech, LLC, Bellevue, WA (US)

( * ) Notice: Subject to any disclaimer, the term of this patent is extended or adjusted under 35 U.S.C. 154(b) by 197 days.

(21) Appl. No.: 09/793,166

(22) Filed: Feb. 26, 2001

(65) Prior Publication Data

US 2001/0015804 A1 Aug. 23, 2001

Related U.S. Application Data

(63) Continuation-in-part of application No. PCT/US99/19986, filed on Aug. 31, 1999.

(51) Int. Cl.[7] .............................. G01N 21/00; H01J 3/14
(52) U.S. Cl. ..................................... 356/241.1; 250/236
(58) Field of Search ........................... 356/241.1–241.6; 250/216, 234–236

(56) References Cited

U.S. PATENT DOCUMENTS

| | | | | |
|---|---|---|---|---|
| 4,440,496 A | * | 4/1984 | Milana | 356/241.1 |
| 4,557,598 A | * | 12/1985 | Ono et al. | 356/241.1 |
| 4,861,984 A | | 8/1989 | West | |
| 5,317,387 A | * | 5/1994 | Van Hengel et al. | 356/625 |

* cited by examiner

Primary Examiner—Michael P. Stafira
(74) Attorney, Agent, or Firm—Graybeal Jackson Haley LLP

(57) ABSTRACT

A device for remote detection of surface flaws in enclosed cavities that have been treated with a photoluminescent medium. The device has a non-rotating ultraviolet radiation source, an offset rotary drive means, a passive rotary scanning means that includes a plurality of lenses, reflectors and an optical filter, a non-rotating solid-state photodiode, and support electronic circuitry. Ultraviolet radiation from the illumination source is projected onto the test-part surface and causes dye penetrant that has been previously deposited onto the test-part surface to fluoresce at a different wavelength, thus revealing the presence of surface cracks and flaws. The receiving lenses capture the fluorescent light and project it onto the photodiode, which generates a series of electrical pulses that correspond to the presence of surface flaws. By encoding the linear and angular position of the scanning means, an accurate and quantitative map of the flaw pattern can be constructed.

25 Claims, 5 Drawing Sheets

SCANNING SYSTEM

This is a continuation-in-part of co-pending International Application PCT/US99/1998 filed on Aug. 31, 1999 designating the United States.

BACKGROUND OF THE INVENTION

Fluorescent dye-penetrant inspection has been an established nondestructive testing method for many years. Traditionally, a component is prepared for inspection by exposing the surface to a low-viscosity fluid that acts as a carrier for a tracer material. As a result of interfacial tension and adsorption, the liquid penetrates into even the smallest surface-breaking cracks and voids. When exposed to ultraviolet light (300 nm to 400 nm wavelength) the tracer material fluoresces at a visible wavelength, thus revealing the presence of indications such as surface-breaking cracks and voids. The most common method for evaluating these indications is through visual observation.

A significant benefit of liquid-penetrant testing is its sensitivity to very small cracks. Surface-breaking cracks as small as a few microns in length can be detected using this nondestructive testing method. Efforts have been undertaken to extend the process of fluorescent dye-penetrant testing to the internal surfaces of critical components such as nuclear steam-generator tubes. These devices use fiber-optic imaging probes and endoscopes, as described in Olympus Corporation, U.S. Pat. No. 5,115,136 and Commissariat a I'Energie Atomique, U.S. Pat. No. 4,791,293, with a right-angle mirror, which "pipe" the two-dimensional image from the tube surface to a remote viewing station using an optical fiber or fiber bundle. In order to rotate the observation assembly, the fiber-optic bundle must include a complex and signal-degrading optical slipring.

Commercial forward-viewing video probes that employ a miniature CCD camera (Welch Allyn, Inc., U.S. Pat. No. 5,202,758) also have been adapted for remote inspection of tubes and pipes that have been treated with dye-penetrant, again using a right-angle mirror to view the test-part surface. Because the two-dimensional image of the cylindrical part surface is obtained using a right-angle mirror, the image is distorted and difficult to interpret visually. These devices do not employ a slipring because of the combination of optical fibers (for light transmission to the tube) and electrical wires (for transmission of the electrical signals from the CCD camera to an external viewing monitor). Inspection is typically a slow process that requires an operator to manipulate the probe manually to various regions of the tube. The two-dimensional image typically is stored to video tape for visual evaluation or, in some cases, image-processing. However, efforts to automate the process through complex image-processing methods have largely proven excessively expensive and unreliable.

Although conventional fluorescent dye-penetrant testing is well accepted and has been in use for years, it is labor-intensive, time-consuming and difficult to convert the complex visual images into quantitative data in a cost-effective manner. Another method for remote nondestructive testing of tubular components using dye-penetrant has been developed by a Sweden-based organization (iP-TEC). As described in U.S. Pat. No. 5,554,800 the system provides a means for treating a surface deep within a steam-generator (or other tube) with photoluminescent dye-penetrant liquid. A plastic plug is then placed in physical contact with the area of concern and any penetrant that has wicked into a crack will be absorbed into the plug, thus creating a precise physical replica of the feature. The plug must then be removed manually from the delivery probe and exposed to UV light in a special viewing device. Features then can be measured manually, photographed and archived. A significant drawback associated with this system is the requirement for manual replacement of the replica plug. This is a significant problem when operating in radiation environments found in nuclear generating stations because it is time-consuming, labor-intensive and exposes the operators to radiation.

SUMMARY OF THE INVENTION

An important aspect of this invention is its use of a non-rotating illumination source and a non-rotating photodiode assembly, cooperating with a rotating passive optical scanning mirror assembly, thus eliminating the need for complex, expensive and signal-degrading sliprings. The ultraviolet illumination source and photodiode are mounted on-axis and do not rotate. De-coupling these two elements from the rotating components of the scanning probe eliminates the need to use electrical or optical sliprings to "pipe" a complex two-dimensional visual image out of the probe via optical fibers. These fundamental differences provide substantial improvement and advantage over conventional video- and fiber-optic- based viewers, including dye-penetrant scanning systems.

The preferred scanning system described herein provides an automated means of rapidly and accurately inspecting a tube, pipe, or other cylindrical or enclosed cavity that have been treated with a photoluminescent penetrant medium. The invention includes: 1) a means of delivering ultraviolet radiation to the test-part surface; 2) a passive rotary scanning means that includes a plurality of lenses, reflectors and an optical filter; 3) an offset rotary drive means that is capable of causing the scanning means to rotate at up to several thousand revolutions per minute; 4) a solid-state photodiode that receives fluorescent light and transmits electrical signals that correspond to the presence of photoluminescent penetrant; and 5) an instrumentation station that provides a means to post-process the signals and a means of evaluating and displaying the condition of the part being inspected.

The passive optical scanning means is caused to rotate by the offset rotary drive means. Ultraviolet radiation from the illumination source is projected on-axis into the optical scanning means. A plurality of lenses focuses the radiation, and a reflecting prism directs the radiation onto the part surface. The result is a concentration of the ultraviolet radiation energy into a very small area (approximately 0.25 $mm^2$). If the ultraviolet radiation strikes dye-penetrant that has been adsorbed into a crack or void, the penetrant will be caused to fluoresce at a visible wavelength.

The receiving lenses, also contained in the passive optical scanning means, capture the fluorescent radiation emanating from the test-part surface and project it through an optical filter and onto the photodiode. A series of electrical pulses corresponding to the presence of surface flaws is generated from the photodiode. The electrical signals are then ported out of the probe to signal-processing instrumentation, via electrical wires, and digitized for further processing. The optical scanning assembly is rotated and translated along the axis of the tube or pipe that is being inspected, creating a helical map of the part surface. By encoding the linear and angular position of the scanning means, an accurate and quantitative map of the digitized flaw pattern can be constructed.

DETAILED DESCRIPTION OF THE PREFERRED EMBODIMENT

Figure 1:
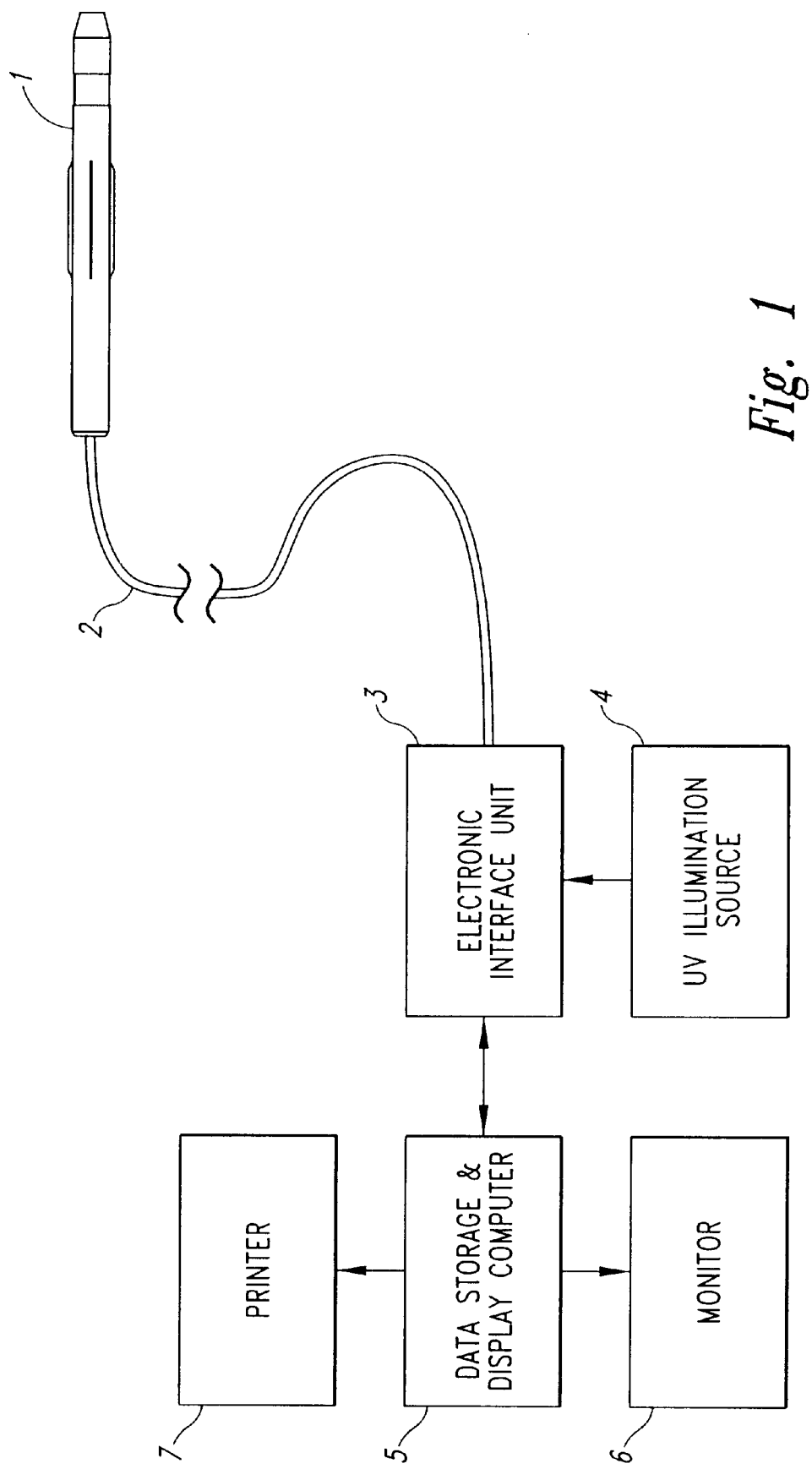
FIG. 1 is a diagrammatic view of the dye-penetrant scanning system in accordance with the invention.

FIG. 1 is a diagrammatic view of the dye-penetrant scanning system in accordance with the invention. This device can be used for the inspection of a wide variety of critical applications, including nuclear steam-generator tubes, turbine rotor bores, aircraft landing gear and automotive parts. The scanning probe 1 can be configured in both straight and articulated forms, in order to facilitate the inspection of bent tubing, e.g. tubing commonly found in nuclear power-generating reactors. Heretofore, remotely operated dye-penetrant inspection systems have employed endoscopes or video probes that require subjective interpretation of the inspection results. The invention described herein provides a significant improvement by employing a high-speed, passive scanner that generates a digital stream of data that can be automatically processed in near real-time by computer means to generate a high-resolution and quantitative map of the test-part surface.

The invention can be used on any tube, pipe and other cylindrical or enclosed cavity surface that has been properly treated with commercial photoluminescent, or other medium, that will adsorb into minute cracks and fluoresce at a wavelength that is different from that to which it has been exposed, e.g. ultraviolet light. Proper surface preparation methods are described in *MIL-STD-6866: Military Standard Inspection Liquid-penetrant and ASTM-E-1417:Practice for Liquid-penetrant Examination*. A preferred commercial penetrant delivery system is manufactured by iP-TEC of Varberg, Sweden.

Figure 2:
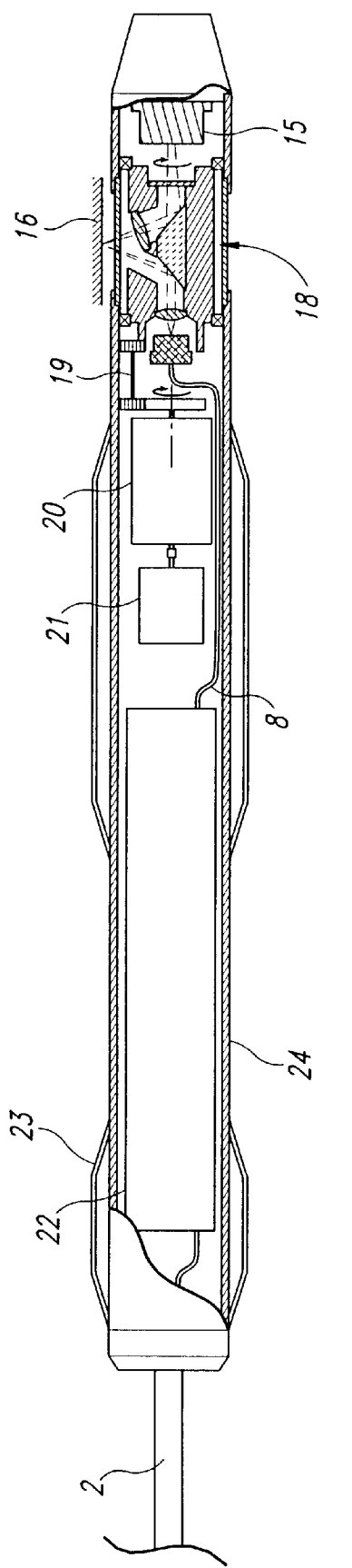
FIG. 2 is a cross-sectional view showing the major components and subassemblies of the scanning probe used in the system of the invention.

The penetrant scanning system shown in FIG. 1 includes a scanning probe 1 that is attached by means of a flexible delivery cable 2 to an electronic interface unit 3. The interface unit 3 is, in turn, attached via electrical cable to a computer 5, which provides control signals for scanning-probe 1 functions. The data storage and display computer 5 also receives, processes and stores inspection data that have been acquired by the scanning probe 1. An ultraviolet illumination source 4 is connected to the interface unit 3 via both electrical wires and an optical fiber (see FIGS. 2 and 3). This optical fiber is then routed to the scanning probe 1 via the delivery cable 2 for the purpose of providing ultraviolet radiation to the optics assembly 18 (FIG. 2). Also shown in FIG. 1 is a computer monitor 6, which is used for operator interface, and a printer 7 for generating hard-copy display of inspection results.

A probe delivery system, various types of which are known per se, provides the axial locomotion for the scanning probe 1. For applications such as tubing inspection, commercially available delivery systems, or so-called "probe pushers" may be used. The only requirement is that the probe pusher be compatible with the delivery cable 2 size and that an axial encoder signal be provided to the interface unit 3 in a compatible format via electrical cable. For non-standard applications a probe delivery system will be required that meets the aforementioned requirements.

FIG. 2 shows a cross-sectional view of the major components and subassemblies of the preferred embodiment of the scanning probe 1 used in the system of the invention. Centering devices 23 keep the scanning probe 1 near the centerline of a cylindrical test-part. The centering devices 23 shown in FIG. 2 are composed of spring wires that are radially oriented about the probe housing 24; however, various types are known per se. The optical fiber 8 transmits ultraviolet radiation from the ultraviolet illumination source 4 to the optics assembly 18. The optics assembly 18 houses a plurality of optical components that are combined to form a means for transmission of optical radiation onto the test-part surface 16 and fluorescent radiation from the test-part surface 16 onto the photodiode 15. Because there are no active electronic or electro-optic components in this self-contained assembly, it is referred to as a passive optics assembly 18. The optics assembly 18 is caused to rotate, relative to the optical fiber 8 and photodiode 15, by the drive motor 20 and offset drive 19 means. An angular encoder 21 monitors the angular position of the optics assembly 18. The offset drive 19 is instrumental in allowing the invention to function properly because the design relies on its ability to transmit ultraviolet radiation into the optics assembly 18 on-axis, and focus the resulting fluorescent radiation, on-axis, onto the photodiode 15. An amplifier circuit 22 in the scanning probe 1 converts the electrical current that is generated by the photodiode 15 to voltage signals, which are then amplified for transmission to the interface unit 3 via the delivery cable 2.

Figure 3A:
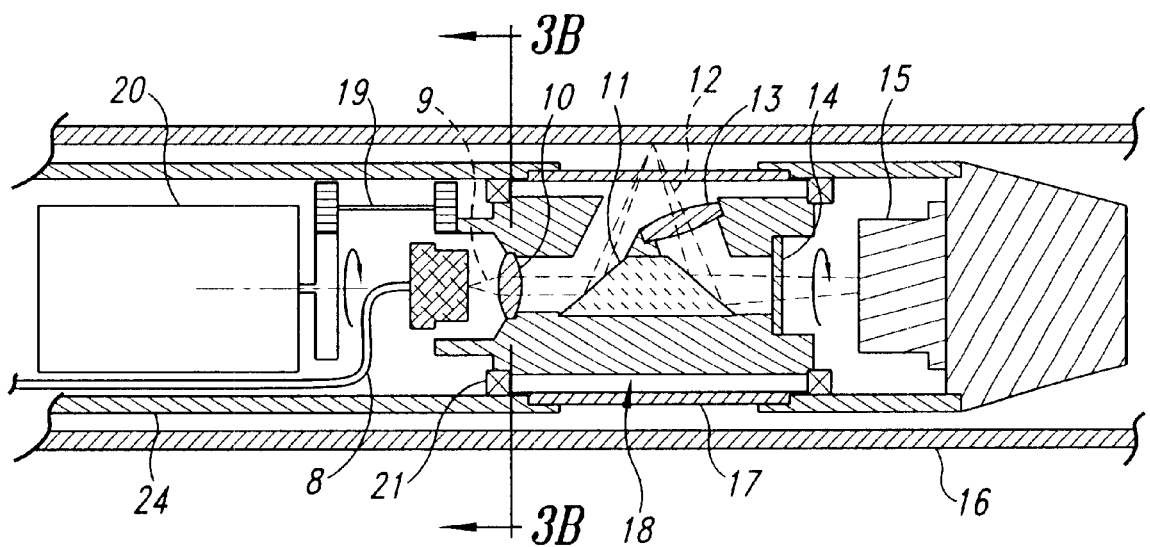
FIGS. 3A and 3B are cross-sectional views showing details of the scanning probe used in the system of the invention.
Figure 3B:
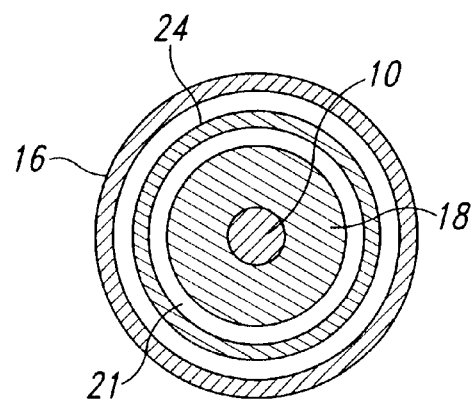

FIGS. 3A and 3B are cross-sectional views showing in more detail the components of the scanning probe 1 used in the system of the invention. Ultraviolet radiation 9 enters the optics assembly 18 via the optical fiber 8, along the mechanical centerline of the scanning probe 1. The ultraviolet radiation 9 is focused by the transmit lens 10 and then redirected through the transparent window 17 and onto the test-part surface 16 by the reflecting mirror 11. The reflecting mirror 11 is a single-element glass prism that has been coated on two surfaces with a suitable reflecting medium, such as gold.

If any surface-breaking cracks or voids are present on the test-part surface 16, the photoluminescent penetrant will respond to exposure to ultraviolet radiation 9 by fluorescing at a different wavelength. The receive lens 13, also contained in the passive optics assembly 18, captures any fluorescent radiation 12 emanating from cracks or voids on the test-part surface 16 and projects it onto the reflecting mirror 11, which redirects it through the optical filter 14 and onto the photodiode 15. The optical filter 14 is designed to block any optical radiation that is the same wavelength as the illumination source 23, e.g. in this case 300 to 400 nm (ultraviolet). Only light resulting from the fluorescent reaction of the dye-penetrant, e.g. greater than 400 nm, can pass through to the photodiode 15. The photodiode 15 is mounted rigidly in the scanning probe 1 on its mechanical centerline and does not rotate. When photons, in the form of fluorescent radiation 12, strike the photodiode 15, minute electrical currents are generated that are proportional to the magnitude of the received energy. An amplifier circuit 22 in the scanning probe 1 converts the electrical currents to voltage signals, which are then amplified for transmission to the interface unit 3. Very fine wires (not shown) connect the photodiode 15 to the amplifier circuit 22. The wires are attached to the transparent window 17 and are not in the focal plane of the projected or received light. Therefore the wires do not negatively effect the transmitted or received light.

Figure 4:
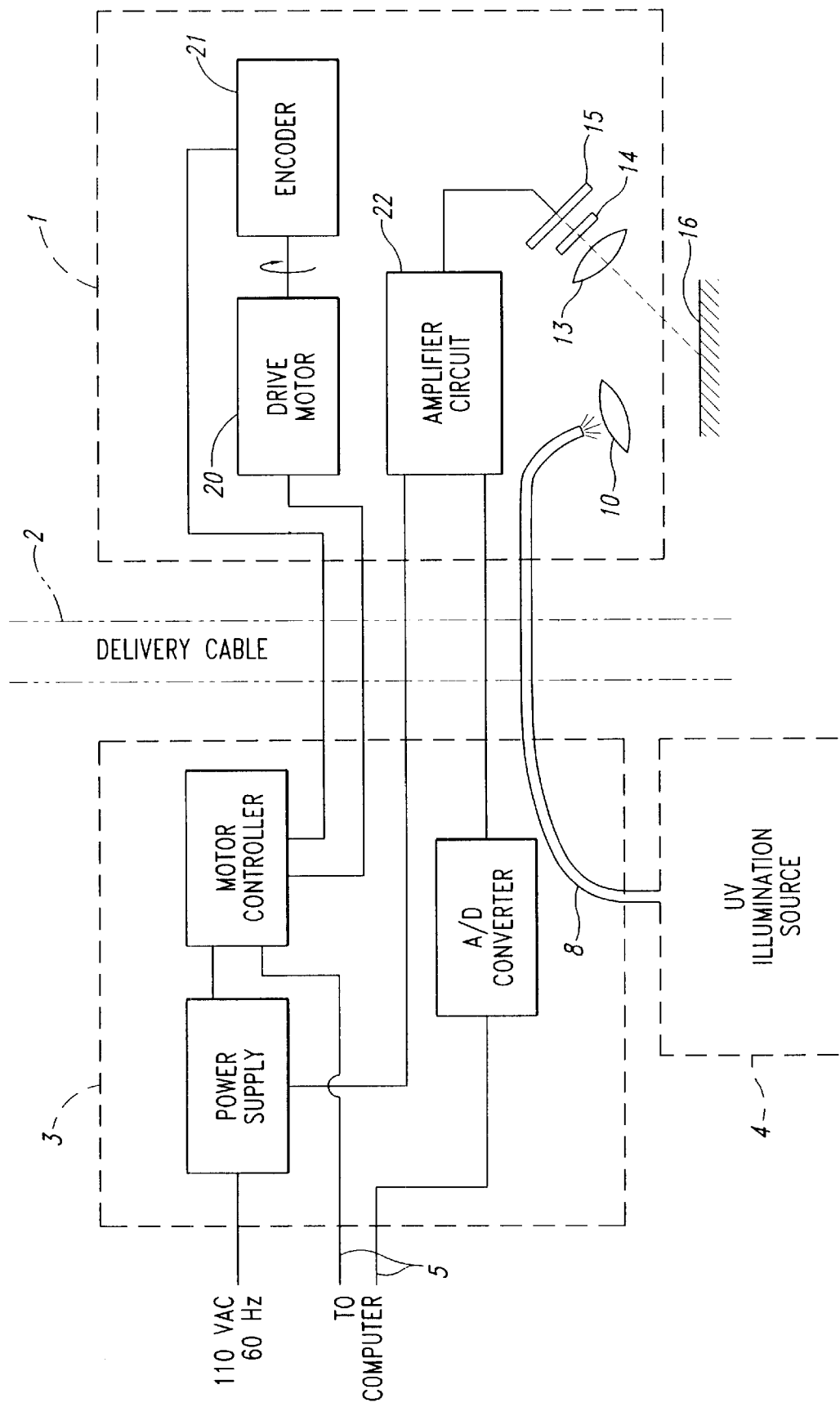
FIG. 4 shows a basic diagram of the electronics and signal-processing details in the system of the invention.

FIG. 4 shows a block diagram of the electronics and signal-processing details in the system. As the scanning probe I rotates and is drawn through a test-part, the electrical signals that are generated from the photodiode 15 correspond to the presence of surface flaws. These electrical signals are then ported out of the scanning probe 1 via the delivery cable 2, to the electronic interface unit 3 and computer 5 for processing, analysis and display. Because the optics assembly 18 is not connected to any part of the scanning probe I by any means other than bearings 21, it can be rotated at very high rates of speed. For example, depending on the application, the optics assembly 18 would be expected to rotate at speeds of 500 to 1,000 revolutions per minute. During normal operation the scanning probe 1 is translated along the axis of the tube or pipe that is being inspected, creating a digital helical map of the test-part surface 16. Encoding the linear and angular position of the optics assembly 18 produces an accurate and quantitative map of the flaw pattern.

Figure 5:
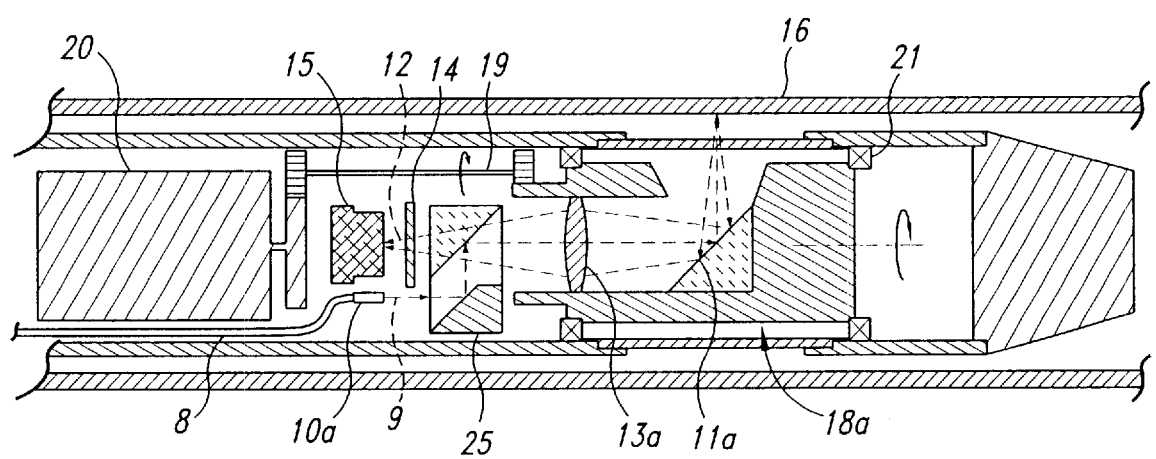
FIG. 5 shows another embodiment of the scanning probe used in the system of the invention.

FIG. 5 shows another embodiment of the scanning probe used in the system of the invention. This configuration eliminates the need to run fine wires through the optical path of the transmitted and received radiation. The optical fiber 8 is located off-axis and, using a transmit lens 10a, projects ultraviolet radiation 9 through a beam-splitter 25 on-axis through the receive lens 13a. The ultraviolet radiation 9 is then reflected by a 450 first-surface reflecting mirror 11a onto the test part surface 16.

Fluorescent radiation 12 emanating from cracks or voids on the test-part surface 16 strikes the reflecting mirror 11a, and is redirected through the receive lens 13a, beam splitter 25, optical filter 14 and onto the photodiode 15. The optical filter 14, also described above, is designed to block any optical radiation that is the same wavelength as the illumination source 23, e.g. in this case 300 to 400 nm (ultraviolet). The electrical signals generated by the photodiode 15 are processed as described above.

The apparatus according to the invention provides numerous unique advantages over conventional photoluminescent penetrant viewing devices, because: 1) it is capable of rapidly scanning a part surface and generating a digital stream of data that can be reconstructed by near real-time signal-processing instrumentation to generate a quantitative and accurate map of surface-breaking flaws; 2) the use of a passive rotating optics assembly eliminates the need for complex and costly optical sliprings; 3) the use of a solid-state photodiode and associated support circuitry provides a high-quality signal that is not subject to the attenuation that is inherent in optical fiber systems.

The apparatus has numerous and varied applications that can be extended to industries including aerospace, chemical and petrochemical processing, nuclear and fossil power generation, automotive manufacturing and testing. The invention also has potential applications in the manufacture and testing of military items such as gun tubes.

In summary, various embodiments of the invention have been disclosed, including a method and apparatus for remote and automatic detection of surface flaws in tubes, pipes and other cylindrical or enclosed cavities that have been treated with a photoluminescent medium. The device, or so-called scanning probe, has a non-rotating ultraviolet radiation source, an offset rotary drive means, a passive rotary scanning means that includes a plurality of lenses, reflectors and an optical filter, a non-rotating solid-state photodiode and support electronic circuitry. The ultra violet illumination source and photodiode are mounted on-axis and do not rotate. A passive optical scanning means is caused to rotate by an offset rotary drive means. Ultraviolet radiation from the illumination source is projected onto the test-part surface to fluoresce at a different wavelength, thus revealing the presence of surface cracks and flaws. The receiving lenses, also contained in the passive rotary scanning mechanism, capture the fluorescent light and project it onto the photodiode. The photodiode generates a series of electrical pulses that correspond to the presence of surface flaws. The pulses are then converted to voltage signals, amplified and ported out of the scanning probe to signal-processing means via electrical wires. By encoding the linear and angular position of the scanning means, an accurate and quantitative map of the flaw pattern can be constructed.

What is claimed is:

1. A scanning probe operable to detect surface flaws in a surface of a cavity that has been treated with a detecting compound, the scanning probe comprising:

a housing adapted to be placed in the cavity;

an optical transmitter coupled to the housing, the optical transmitter operable to generate incident optical energy;

a single-element optical receiver coupled to the housing, the optical receiver operable to develop an electrical signal responsive to received secondary optical energy;

an optical assembly coupled to the housing and operable to move relative to the optical transmitter and optical receiver, the optical assembly focusing incident optical energy from the optical transmitter and applying focused optical energy onto a location on the surface of the cavity, the location being a function of the position of the optical assembly relative to the optical transmitter, and the optical assembly applying to the optical receiver secondary optical energy radiated from the location in response to the applied focused optical energy; and a driver coupled to the housing and coupled to the optical assembly, the driver positioning the optical assembly to sequentially apply focused optical energy on respective locations on the surface of the cavity to thereby cause the optical receiver to generate a series of the electrical signals responsive to secondary optical energy radiated from the respective locations, the driver also developing a series of position signals, each position signal indicating the position of the respective location at which the focused optical energy is applied, and the combination of the series of electrical signals and position signals forming a flaw map that provides information about the location of any defects present on the surface of the cavity.

2. The scanning probe of claim 1 wherein the optical assembly is coupled to the housing between the optical transmitter and the optical receiver.

3. The scanning probe of claim 1 wherein the optical transmitter comprises a laser diode that generates ultraviolet optical energy.

4. The scanning probe of claim 1 wherein the single-element optical receiver comprises a photodiode that detects fluorescent radiation emanating from cracks or voids in the surface of the cavity that contain the detecting compound.

5. The scanning probe of claim 1 wherein the housing comprises a cylindrical housing having a longitudinal axis and wherein the driver causes the optical assembly to rotate about the longitudinal axis relative to the optical transmitter and receiver.

6. The scanning probe of claim 5 wherein the optical assembly comprises:
- a transmitting lens positioned adjacent the optical transmitter, the transmitting lens focusing the incident optical energy to a small spot;
- a reflecting mirror positioned adjacent the transmitting lens, the reflecting mirror directing the focused incident optical energy from the transmitting lens onto the surface of the cavity and directing any secondary optical energy in a desired direction;
- a receiving lens positioned adjacent the reflecting mirror to receive secondary optical energy generated responsive to the focused incident optical energy and focus the received secondary optical energy onto the reflecting mirror, the secondary optical energy having a different wavelength than the focused incident optical energy; and
- an optical filter positioned adjacent the reflecting mirror in the desired direction to receive secondary optical energy from the reflecting mirror, the optical filter transmitting optical energy having substantially the wavelength of the secondary optical energy to the optical receiver, and blocking any optical energy not having substantially the wavelength of the secondary optical energy.

7. The scanning probe of claim 6 wherein the driver comprises an offset drive coupled between the optics assembly and the driver, the offset drive rotating the optics assembly responsive to the driver, and the driver including an angular encoder that detects the angular position of the optics assembly and outputs a signal indicating the detected angular position.

8. The scanning probe of claim 7 wherein the driver and offset drive operate to rotate the optics assembly at between approximately 500 and approximately 1000 revolutions per minute.

9. A scanning probe operable to detect surface flaws in an inner surface of a cylindrical cavity that has been treated with a detecting compound, the scanning probe comprising:
- a cylindrical housing adapted to be placed in the cavity, the cylindrical housing including an optical window and having a longitudinal axis;
- an optical transmitter coupled to the housing, the optical transmitter operable to generate incident optical energy;
- a single-element optical receiver coupled to the housing, the optical receiver operable to develop a defect signal responsive to received secondary optical energy; and
- an optical assembly coupled to the housing and operable to rotate about the longitudinal axis, the optical assembly focusing incident optical energy from the optical transmitter and applying focused optical energy from the optical transmitter through the optical window and onto a location on the surface of the cavity, the location being a function of the angular position of the optical assembly, and the optical assembly applying to the optical receiver secondary optical energy radiated from the location through the optical window in response to the applied focused optical energy; and
- a driver coupled to the housing and coupled to the optical assembly, the driver continuously rotating the optical assembly to sequentially apply focused optical energy on respective locations on the surface of the cavity to thereby cause the optical receiver to sequentially generate values of the defect signal responsive to secondary optical energy radiated from the respective locations, the driver also developing a position signal indicating the angular position of the optical assembly, the values of defect signals and the position signal forming a flaw map that provides information about the location of any defects present on the surface of the cavity.

10. The scanning probe of claim 9 wherein the optical assembly is coupled to the housing between the optical transmitter and the optical receiver.

11. The scanning probe of claim 9 wherein the optical transmitter comprises a laser diode that generates ultraviolet optical energy.

12. The scanning probe of claim 9 wherein the single-element optical receiver comprises a photodiode that detects fluorescent radiation emanating from cracks or voids in the surface of the cavity that contain the detecting compound.

13. The scanning probe of claim 9 wherein the optical assembly comprises:
- a transmitting lens positioned adjacent the optical transmitter, the transmitting lens focusing the incident optical energy onto a small area;
- a reflecting mirror positioned adjacent the transmitting lens, the reflecting mirror directing the focused incident optical energy from the transmitting lens onto the surface of the cavity and directing any secondary optical energy in a desired direction;
- a receiving lens positioned adjacent the reflecting mirror to receive secondary optical energy generated responsive to the focused incident optical energy and focus the received secondary optical energy onto the reflecting mirror, the secondary optical energy having a different wavelength than the focused incident optical energy; and
- an optical filter positioned adjacent the reflecting mirror in the desired direction to receive secondary optical energy from the reflecting mirror, the optical filter transmitting optical energy having substantially the wavelength of the secondary optical energy to the optical receiver, and blocking any optical energy not having substantially the wavelength of the secondary optical energy.

14. The scanning probe of claim 13 wherein the driver comprises an offset drive coupled between the optics assembly and the driver, the offset drive rotating the optics assembly responsive to the driver.

15. The scanning probe of claim 14 wherein the driver and offset drive operate to rotate the optics assembly at between approximately 500 and approximately 1000 revolutions per minute.

16. A scanning system, comprising:
- a scanning probe operable to detect surface flaws in a surface of a cavity that has been treated with a detecting compound, the scanning probe comprising:
  - a housing adapted to be placed in the cavity;
  - an optical transmitter coupled to the housing, the optical transmitter operable to generate incident optical energy;
  - a single-element optical receiver coupled to the housing, the optical receiver operable to develop an electrical signal responsive to received secondary optical energy;
  - an optical assembly coupled to the housing and operable to move relative to the optical transmitter and optical receiver, the optical assembly focusing incident optical energy from the optical transmitter and applying focused optical energy onto a location on the surface of the cavity, the location being a function of the position of the optical assembly relative to the optical transmitter, and the optical assembly applying to the optical receiver secondary optical energy radiated from the location in response to the applied focused optical energy; and a driver coupled to the housing and coupled to the optical assembly, the driver positioning the optical assembly to sequentially apply focused optical energy on respective locations on the surface of the cavity to thereby cause the optical receiver to generate a series of the electrical signals responsive to secondary optical energy radiated from the respective locations, the driver also developing a series of position signals, each position signal indicating the position of the respective location at which the focused optical energy is applied, and the combination of the series of electrical signals and position signals forming a flaw map that provides information about the location of any defects present on the surface of the cavity;

an electronic interface unit coupled to the scanning probe to receive the electrical signals and position signals and convert these signals to desired logic levels, and the electronic interface unit applying control signals to control the driver and thereby control position of the optical assembly; and a computer system coupled to the electronic interface unit to receive the converted electrical and position signals and applying signals to control operation of the electronic interface unit, the computer system storing values of the electrical and position signals and displaying the stored values as a flaw map.

17. The scanning probe of claim 16 wherein the optical assembly is coupled to the housing between the optical transmitter and the optical receiver.

18. The scanning probe of claim 16 wherein the optical transmitter comprises a laser diode that generates ultraviolet optical energy.

19. The scanning probe of claim 16 wherein the single-element optical receiver comprises a photodiode that detects any fluorescent radiation emanating from cracks or voids in the surface of the cavity that contain the detecting compound.

20. The scanning probe of claim 16 wherein the housing comprises a cylindrical housing having a longitudinal axis and wherein the driver causes the optical assembly to rotate about the longitudinal axis relative optical transmitter and optical receiver.

21. A method of detecting surface flaws in a surface of a cavity that has been treated with a detecting compound, comprising:

applying focused optical energy to a location on the surface of the cavity;

detecting secondary optical energy generated in response to the focused optical energy;

generating an electrical signal responsive to the detected secondary optical energy;

scanning the surface of the cavity by repeating the acts of applying focused optical energy through generating an electrical signal on a plurality of respective locations on the surface to thereby generate a series of values for the electrical signal; and processing the series of values of the electrical signal to detect flaws present on the surface of the cavity.

22. The method of claim 21 wherein applying focused optical energy at the first wavelength comprises applying ultraviolet light to the location on the surface of the cavity.

23. A method of detecting surface flaws in a surface on a cavity that has been treated with a detecting compound, comprising:

applying focused optical energy to a location on the surface of the cavity;

detecting secondary optical energy generated in response to the focused optical energy interacting with the detecting compound;

generating an electrical signal responsive to the detected secondary optical energy;

scanning the surface of the cavity by repeating the acts of applying focused optical energy through generating an electrical signal on a plurality of respective locations on the surface to thereby generate a series of values for the electrical signal; and processing the series of values of the electrical signal to detect flaws present on the surface of the cavity;

wherein detecting secondary optical energy comprises detecting the fluorescence of the detecting compound that has penetrated into any surface cracks or voids in the surface of the cavity at the location.

24. A method of detecting surface flaws in a surface on a cavity that has been treated with a detecting compound comprising:

applying focused optical energy to a location on the surface of the cavity;

detecting secondary optical energy generated in response to the focused optical energy interacting with the detecting compound;

generating an electrical signal responsive to the detected secondary optical energy;

scanning the surface of the cavity by repeating the acts of applying focused optical energy through generating an electrical signal on a plurality of respective locations on the surface to thereby generate a series of values for the electrical signal; and processing the series of values of the electrical signal to detect flaws present on the surface of the cavity;

wherein processing the series of values of the electrical signal comprises:
storing the series of values of the electrical signal; and
storing for each value of the electrical signal an angular and a linear position of the location on the surface of the cavity where the focused optical energy was applied, the combination of stored values of the electrical signal and angular and linear positions forming a flaw map of the surface of the cavity.

25. The method of claim 21 wherein the surface of the cavity comprises a cylindrical surface and scanning the surface of the cavity comprises a rotational scan of the cylindrical surface.

* * * * *

UNITED STATES PATENT AND TRADEMARK OFFICE
CERTIFICATE OF CORRECTION

PATENT NO. : 6,633,378 B2
DATED : October 14, 2003
INVENTOR(S) : James L. Doyle, Jr.

It is certified that error appears in the above-identified patent and that said Letters Patent is hereby corrected as shown below:

<u>Column 9,</u>
Line 55, after "energy", please insert -- at a first wavelength --.
Line 57, after "generated", please insert -- at a second wavelength --.
Line 58, after "energy", please insert -- interacting with the detecting compound --.

<u>Column 10,</u>
Line 9, please replace "on" with -- of --.
Line 31, please replace "on" with -- of --.

Signed and Sealed this

Tenth Day of February, 2004

JON W. DUDAS
*Acting Director of the United States Patent and Trademark Office*